(12) United States Patent
Hauck et al.

(10) Patent No.: US 8,700,129 B2
(45) Date of Patent: Apr. 15, 2014

(54) DEVICES AND METHODS FOR CATHETER LOCALIZATION

(75) Inventors: John A. Hauck, Shoreview, MN (US); Lubomir V. Dragnev, Little Canada, MN (US); D. Curtis Deno, Andover, MN (US); Eric J. Wilkowske, North Oaks, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1355 days.

(21) Appl. No.: 12/347,271

(22) Filed: Dec. 31, 2008

(65) Prior Publication Data

US 2010/0168560 A1    Jul. 1, 2010

(51) Int. Cl.
*A61B 5/05* (2006.01)
*A61B 5/06* (2006.01)

(52) U.S. Cl.
USPC .......................................... 600/424; 600/508

(58) Field of Classification Search
USPC ........................ 600/508, 547, 427; 607/2, 122
See application file for complete search history.

(56) References Cited

U.S. PATENT DOCUMENTS

| | | | |
|---|---|---|---|
| 5,385,148 A | 1/1995 | Lesh et al. | |
| 5,391,199 A | 2/1995 | Ben-Haim | |
| 5,480,422 A | 1/1996 | Ben-Haim | |
| 5,546,951 A | 8/1996 | Ben-Haim | |
| 5,568,809 A | 10/1996 | Ben-Haim | |
| 5,662,108 A | 9/1997 | Budd et al. | |
| 5,694,945 A | 12/1997 | Ben-Haim | |
| 5,697,377 A | 12/1997 | Wittkampf | |
| 5,713,946 A | 2/1998 | Ben-Haim | |
| 5,718,241 A | 2/1998 | Ben-Haim et al. | |
| 5,840,025 A | 11/1998 | Ben-Haim | |
| 5,944,022 A * | 8/1999 | Nardella et al. | 128/899 |
| 5,983,126 A | 11/1999 | Wittkampf | |
| 6,216,027 B1 * | 4/2001 | Willis et al. | 600/424 |
| 6,277,077 B1 | 8/2001 | Brisken et al. | |
| 6,640,119 B1 | 10/2003 | Budd et al. | |
| 6,728,562 B1 | 4/2004 | Budd et al. | |

(Continued)

OTHER PUBLICATIONS

Desai JM, Nyo HL, Vera Z, et al., "Two Phase Radiofrequency Ablation of Isolated Ventricular Endocardium", PACE 1991; 14:1179-1194.

(Continued)

*Primary Examiner* — Long V. Le
*Assistant Examiner* — Bradley Impink
(74) *Attorney, Agent, or Firm* — Wiley Rein LLP

(57) ABSTRACT

A medical device can be localized by providing at least three non-colinear localization elements (e.g., electrodes) thereon. Once placed in a non-ionizing localization field, three adjacent localization elements, at least one of which will typically be a spot electrode, may be selected, and the non-ionizing localization field may be used to measure their locations. A cylinder is defined to fit the measured locations of the selected localization elements. The cylinder is rotationally oriented using the measured location of a spot electrode. Location and rotational attitude information may be used to construct a three-dimensional representation of the medical device within the localization field. The electrodes may be provided on the medical device or on a sheath into which the medical device is inserted. The invention also provides systems and methods for identifying and calibrating deflection planes where the medical device and/or sheath are deflectable.

24 Claims, 5 Drawing Sheets

(56) References Cited

U.S. PATENT DOCUMENTS

| | | |
|---|---|---|
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 2002/0060833 A1 | 5/2002 | Yamaguchi |
| 2003/0050557 A1* | 3/2003 | Susil et al. .................. 600/424 |
| 2004/0254437 A1 | 12/2004 | Hauck et al. |
| 2005/0137478 A1 | 6/2005 | Younge et al. |
| 2005/0222554 A1 | 10/2005 | Wallace et al. |
| 2006/0095022 A1 | 5/2006 | Moll et al. |
| 2006/0100610 A1 | 5/2006 | Wallace et al. |
| 2008/0249395 A1* | 10/2008 | Shachar et al. ............... 600/409 |
| 2009/0253985 A1* | 10/2009 | Shachar et al. ............... 600/424 |

OTHER PUBLICATIONS

Desai JM, Nyo HL, Vera Z, et al., "Orthogonal Electrode Catheter Array for Mapping of Endocardial Focal Site of Ventricular Activation", PACE 1991 Part I; 14:557-574.

Rosborough, John P., et al., "A Percutaneous Catheter-Based System for the Measurement of Potential Gradients Applicable to the Study of Transthoracic Defibrillation", PACE 2007; 30:166-174.

Wittkampf, Fred HM, et al., "LocaLisa : New Technique for Real-Time 3-Dimensional Localization of Regular Intracardiac Electrodes", Circulation 2009; 1311-1317.

Earley, Mark J., et al., "Radiofrequency ablation of arrhythmias guided by non-fluoroscopic catheter location: a prospective randomized trial", European Heart Journal 2006; 27:1223-1229.

* cited by examiner

DEVICES AND METHODS FOR CATHETER LOCALIZATION

BACKGROUND OF THE INVENTION a. Field of the Invention

The instant invention relates to systems that measure position and orientation of medical devices. In particular, the instant invention relates to systems and methods for measuring the position and orientation of a medical device within a non-ionizing localization field.

b. Background Art

It is well known how to generate heart chamber geometry in preparation for cardiac diagnostic or therapeutic procedures. Often, a mapping catheter is introduced into the heart chamber of interest and moved around within the heart chamber, either randomly, pseudo-randomly, or according to one or more preset patterns. The three-dimensional coordinates are measured using a localization system (sometimes also referred to as a "mapping system," "navigation system," or "positional feedback system"). The localization system measures the coordinates of the mapping catheter within a localization field, typically by relating a characteristic of the localization field, such as a voltage, experienced by the mapping catheter to a location of the catheter within the field.

A similar process may be used to measure the position of any object, such as an ablation catheter or other medical device, within the localization field. Such devices may be steerable, for example through the use of one or more pull wires that, when placed in tension, deflect the distal end of the device. Often, the deflection plane or planes of such devices are determined through trial and error—that is, the practitioner deflects the catheter and views the deflection on a display connected to the localization system. When the device is rotated, the practitioner may need to repeat this trial and error process. For more advanced steerable devices including multiple pull wires that permit deflection in a greater number of planes, a trial and error approach to identifying deflection planes can be very time consuming and inefficient.

BRIEF SUMMARY OF THE INVENTION

It is desirable to be able to localize (that is, identify the position and rotational attitude) of a medical device within a localization field. These devices may or may not include localization elements, such as localization electrodes, as manufactured.

It is also desirable to be able to calibrate a deflectable medical device so as to predict the deflection that will result from a particular input.

Disclosed herein is a method of localizing a medical device including the steps of: providing an elongate medical device having a diameter and at least three non-colinear localization electrodes mounted thereon; placing the elongate medical device within a non-ionizing localization field; selecting three adjacent localization electrodes of the at least three non-colinear localization electrodes, the selected three localization electrodes including a proximal ring localization electrode, a distal ring localization electrode, and a third localization electrode; using the non-ionizing localization field to measure a location of each of the selected three localization electrodes; defining a cylinder having a central axis connecting the measured locations of the proximal and distal ring localization electrodes and a diameter equal to the diameter of the elongate medical device; projecting the measured location of the third localization electrode orthogonally to a surface of the defined cylinder; defining an orienting stripe parallel to the central axis of the defined cylinder and passing through the projected location of the third localization electrode; and constructing a three-dimensional representation of the elongate medical device within the localization field. In a preferred embodiment of the invention, the third localization electrode is an intermediate localization electrode positioned between the proximal ring electrode and the distal ring electrode. Optionally, the three-dimensional representation of the elongate medical device within the localization field may be output on a display.

The step of using the non-ionizing localization field to measure a location of each of the selected three localization electrodes may include determining a position of a center of the proximal ring localization electrode and a position of a center of the distal ring localization electrode.

In some embodiments of the invention, the step of providing an elongate medical device includes: providing an elongate medical device; providing a localization sheath having at least three non-colinear localization electrodes mounted thereon; and placing the elongate medical device within the localization sheath. Optionally, the localization sheath may be affixed to the elongate medical device, such as by expanding and softening the localization sheath using a solvent, placing the elongate medical device within the localization sheath, and then evaporating the solvent. Alternatively, the localization sheath may be bonded to the medical device, such as through the use of an ultraviolet-activated adhesive. In still other embodiments, the localization sheath may be laminated to the medical device via the application of heat.

Either the localization sheath or the elongate medical device may include at least one actuator configured to deflect the localization sheath or medical device along at least one plane. The actuator may be calibrated through the following process: actuating the elongate medical device to deflect; measuring a deflected location of each of the proximal and distal ring localization electrodes; defining a deflected axis connecting the measured deflected locations of the proximal and distal ring localization electrodes; defining a deflection plane using the central axis of the defined cylinder and the deflected axis; and defining a deflection plane stripe where the deflection plane intersects the surface of the defined cylinder. Once the actuator is calibrated, it may be marked with a reference corresponding to the deflection plane. Further, the deflection plane stripe may be displayed as part of the three-dimensional representation of the elongate medical device within the localization field, with the displayed deflection plane stripe corresponding to the marking on the at least one actuator (e.g., a green marking on the actuator corresponds to a green deflection plane stripe displayed as part of the three-dimensional representation).

It is contemplated that the steps of actuating the elongate medical device to deflect, measuring a deflected location of each of the proximal and distal ring localization electrodes, defining a deflected axis connecting the measured deflected locations of the proximal and distal ring localization electrodes, defining a deflection plane using the central axis of the defined cylinder and the deflected axis, and defining a deflection plane stripe where the deflection plane intersects the surface of the defined cylinder may be repeated to define a plurality of deflection plane stripes for a plurality of user-defined deflection planes.

In another aspect, the present invention provides a method of localizing a medical device including the steps of: providing an elongate medical device having at least three non-colinear localization elements mounted thereon; placing the elongate medical device within a non-ionizing localization field; selecting three or more of the non-colinear localization elements, wherein at least one of the selected non-colinear localization elements is a spot localization element; using the non-ionizing localization field to measure a location of each of the selected non-colinear localization elements; constructing a three-dimensional representation of the elongate medical device using the measured location of each of the selected non-colinear localization elements; and rotationally orienting the three-dimensional representation of the elongate medical device using the measured location of the spot localization element.

The step of constructing a three-dimensional representation of the elongate medical device typically includes fitting a cylinder (having a first axis) to the measured location of each of the selected non-colinear localization elements. For example, in some embodiments of the invention, the selected non-colinear localization elements include a distal ring electrode and a proximal ring electrode and the step of fitting a cylinder includes defining a cylinder having a central axis connecting the measured locations of the distal ring electrode and the proximal ring electrode and a diameter equal to a diameter of the elongate medical device.

In some embodiments of the invention, the elongate medical device includes at least one actuator configured to deflect the elongate medical device along at least one plane. The method may then also include the following steps: actuating the elongate medical device to deflect; measuring a deflected location of each of the selected non-colinear localization elements; defining a deflection plane using the measured location and the measured deflected location of each of the selected non-colinear localization elements; and defining a deflection plane stripe on the surface of the three-dimensional representation of the elongate medical device. The step of defining a deflection plane may include: fitting a cylinder to the measured deflected location of each of the selected non-colinear localization elements, wherein the cylinder fit to the measured deflected location of each of the selected non-colinear localization elements has a second axis; and defining a deflection plane using the first axis and the second axis. Further, the step of defining a deflection plane stripe may include defining a deflection plane stripe where the deflection plane intersects the cylinder fit to the measured location of each of the selected non-colinear localization elements. At least one actuator may then be marked with a reference corresponding to the deflection plane.

The step of rotationally orienting the three-dimensional representation may include defining an orienting stripe on a surface of the three-dimensional representation through the measured location of the spot localization element.

The present invention also provides a sheath for use in localizing a medical device. The sheath generally includes: an elongate, flexible sheath body having an open distal end and an open proximal end and defining a lumen sized to conformably receive an elongate medical device; and at least three non-colinear localization elements mounted on the sheath body. The at least three non-colinear localization elements may include a distal ring electrode, a proximal ring electrode, and a spot electrode. Alternatively, the at least three non-colinear localization elements may include at least three non-colinear spot electrodes. For example, the sheath may include at least three pairs of opposing spot electrodes, wherein each of the at least three pairs of opposing spot electrodes has a unique rotational orientation. Of course, other combinations and types of localization elements are contemplated and regarded as within the spirit and scope of the present invention.

In some embodiments of the invention, the sheath body includes an inner layer and an outer layer. At least three non-colinear localization elements may then be sandwiched between the inner layer and the outer layer. By bonding the inner layer to the outer layer, the localization elements (and any associated leads) may be secured.

By way of example, a method of manufacturing a sheath for use in localizing a medical device according to some embodiments of the present invention includes the following steps: forming an inner layer of a flexible material; mounting at least three non-colinear localization elements on the inner layer; forming an outer layer of a flexible material about the inner layer and the at least three non-colinear localization elements; and bonding the outer layer to the inner layer.

In still another aspect, the present invention provides a system for localizing a medical device. The system includes: at least one localization field generator for creating a localization field that can be used for determining a location of an object within the localization field; a localization sheath having at least three non-colinear localization elements mounted thereon; and a localization processor. The localization processor measures a location of three or more of the non-colinear localization elements, including at least one spot localization element; constructs a three-dimensional representation of a medical device using the measured location of the three or more non-colinear localization elements; and rotationally orients the three-dimensional representation using the measured location of the at least one spot localization element.

An advantage of the present invention is that it permits localization (that is, identification of position and rotational attitude) of a medical device within a localization field.

Another advantage of the present invention is that it provides a localization sheath that can be used to endow medical devices with localization capability even if they do not include localization elements, such as localization electrodes, as manufactured.

Still another advantage of the present invention is that it allows for the relationship between actuator inputs and device deflections to be known a priori rather than discovered through trial and error.

Yet another advantage of the present invention is that it permits calibration to occur on arbitrary, user-defined deflection axes instead of requiring prior knowledge of the position of pull wires.

The foregoing and other aspects, features, details, utilities, and advantages of the present invention will be apparent from reading the following description and claims, and from reviewing the accompanying drawings.

DETAILED DESCRIPTION OF THE INVENTION

The present invention provides a method and system for localizing a medical device within a non-ionizing localization field, such as an electric or magnetic field. As used herein, the term "localization" includes both locating (that is, identifying the position of) and orienting (that is, identifying the rotational attitude of) the medical device. Localization fields are often employed in procedures carried out within a human body, and in particular in cardiac diagnostic and therapeutic procedures. Therefore, for purposes of illustration, the invention will be described in detail in the context of a localization system utilized in a cardiac electrophysiology procedure. It is contemplated, however, that the present invention may be practiced to good advantage in other contexts.

Figure 1:
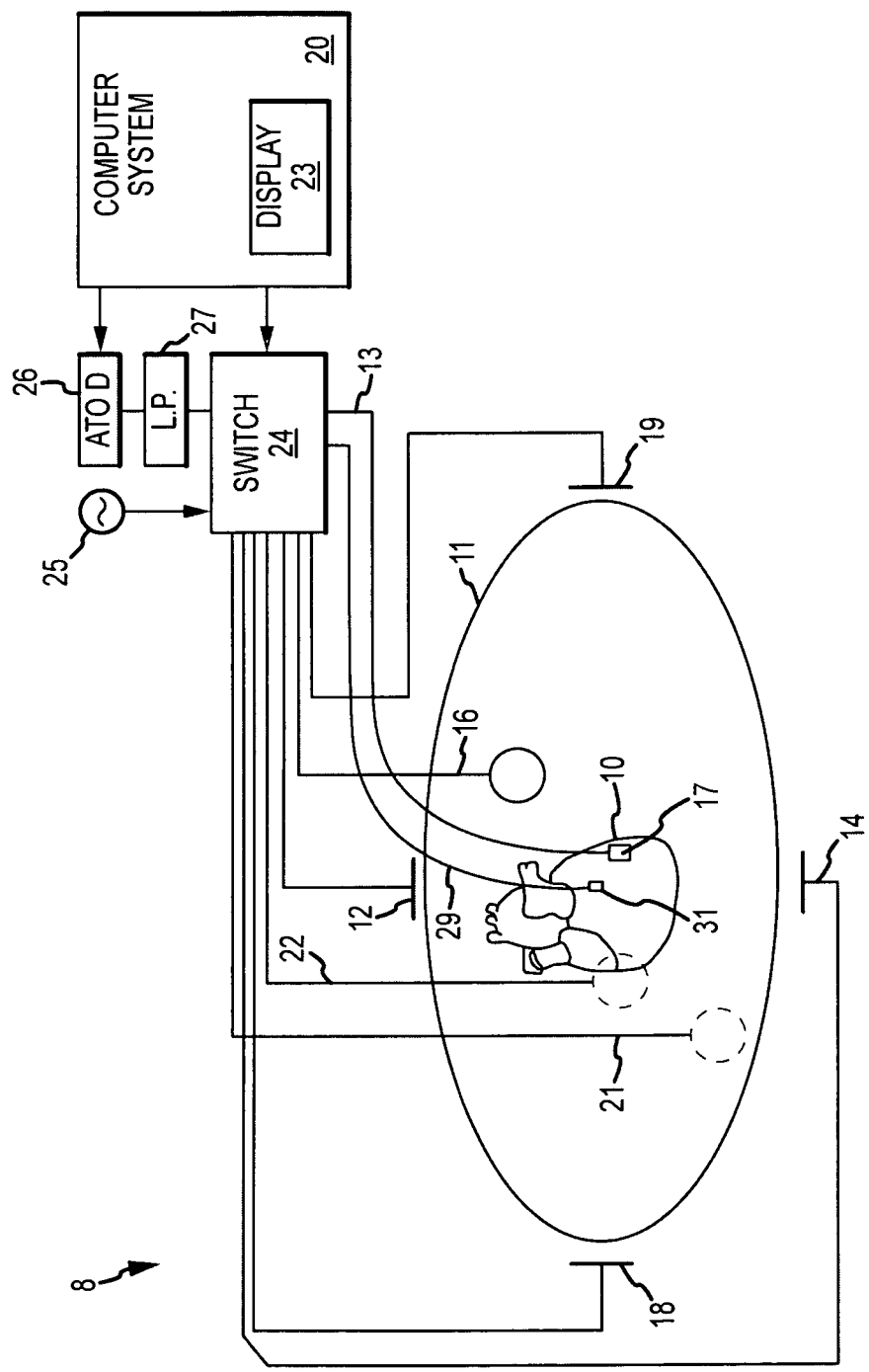
FIG. 1 is a schematic diagram of a localization system utilized in an electrophysiology study.

FIG. 1 shows a schematic diagram of a localization system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface, and store the measured data in association with location information for each measurement point at which the electrophysiology data was measured, for example to create a diagnostic data map of the patient's heart 10. As one of ordinary skill in the art will recognize, and as will be further described below, localization system 8 determines the location of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. Likewise, the electrodes do not need to be on the body surface, but could be fixed on an external apparatus, or electrodes positioned internally to the body could be used.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG") system leads in place. This ECG information is available to the system 8, although not illustrated in FIG. 1.

A representative catheter 13 having at least one electrode 17 (e.g., a distal electrode) is also shown. This representative catheter electrode 17 is referred to as the "roving electrode," "moving electrode," or "measurement electrode" throughout the specification. Typically, multiple electrodes on catheter 13, or on multiple such catheters, will be used. In one embodiment, for example, localization system 8 may comprise sixty-four electrodes on twelve catheters disposed within the heart and/or vasculature of the patient. Of course, this embodiment is merely exemplary, and any number of electrodes and catheters may be used within the scope of the present invention.

Figure 2:
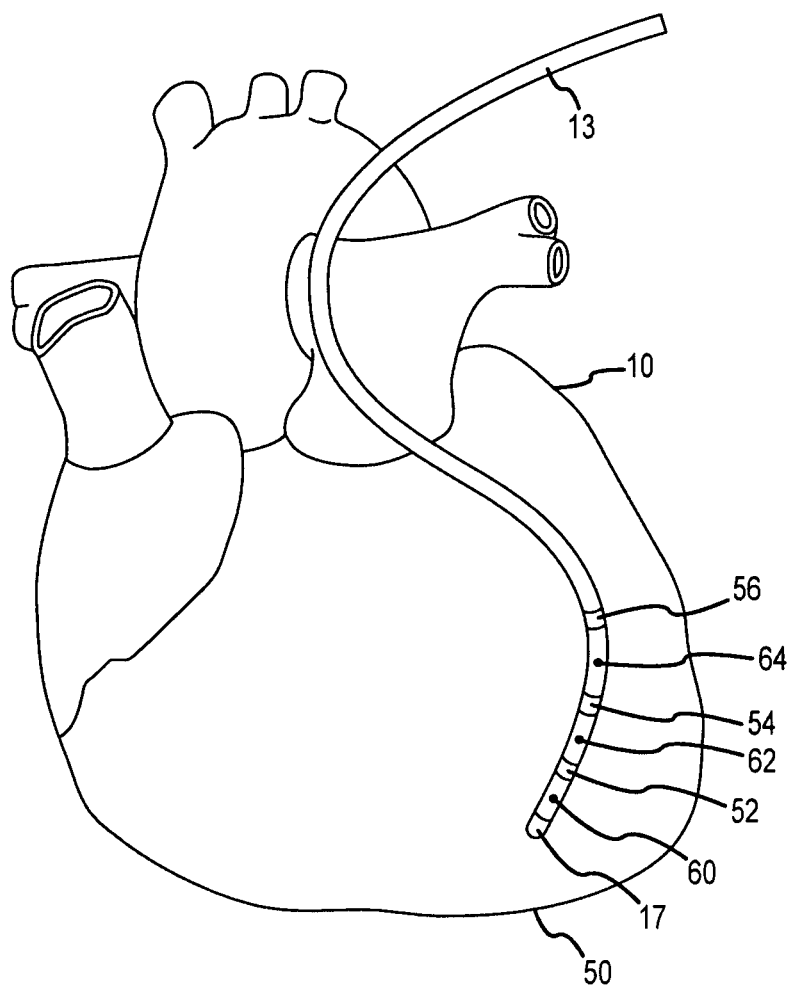
FIG. 2 depicts an exemplary catheter used in an electrophysiology study.

For purposes of this disclosure, an exemplary catheter 13 is shown in FIG. 2. In FIG. 2, catheter 13 extends into the left ventricle 50 of the patient's heart 10. Catheter 13 includes electrode 17 on its distal tip, as well as a plurality of additional measurement electrodes 52, 54, 56 spaced along its length. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by localization system 8.

Returning now to FIG. 1, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to the multiplex switch 24, and the pairs of surface electrodes are selected by software running on a computer 20, which couples the surface electrodes to a signal generator 25. The computer 20, for example, may comprise a conventional general-purpose computer, a special-purpose computer, a distributed computer, or any other type of computer. The computer 20 may comprise one or more processors, such as a single central processing unit (CPU), or a plurality of processing units, commonly referred to as a parallel processing environment, which may execute instructions to practice the various aspects of the present invention described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17, 52, 54, 56 placed in the heart 10 are exposed to the field from a current pulse and are measured with respect to ground, such as belly patch 21. In practice the catheters within the heart may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the roving electrodes 17, 52, 54, 56 within heart 10.

The measured voltages may be used to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. Preferably, the coordinate system is a three-dimensional (x, y, z) Cartesian coordinate system, though the use of other coordinate systems, such as polar, spherical, and cylindrical coordinate systems, is within the scope of the invention.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Patent Application Publication No. 2004/0254437, which is hereby incorporated herein by reference in its entirety. The electrode data may also be used to compensate for changes in the impedance of the body of the patient as described in co-pending U.S. patent application Ser. No. 11/227,580, filed on 15 Sep. 2005, which is also incorporated herein by reference in its entirety.

In summary, the system 8 first selects a set of surface electrodes and then drives them with current pulses. While the current pulses are being delivered, electrical activity, such as the voltages measured at least one of the remaining surface electrodes and in vivo electrodes, is measured and stored. Compensation for artifacts, such as respiration and/or impedance shifting, may be performed as indicated above.

In a preferred embodiment, the localization/mapping system is the EnSite NavX™ navigation and visualization system of St. Jude Medical, Atrial Fibrillation Division, Inc., which generates the electrical fields described above. Other localization systems, however, may be used in connection with the present invention, including for example, the CARTO navigation and location system of Biosense Webster, Inc., the AURORA® system of Northern Digital Inc., or Sterotaxis' NIOBE® Magnetic Navigation System, all of which utilize magnetic fields rather than electrical fields. The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

The fields generated by localization system 8, whether an electrical field (e.g., EnSite NavX™), a magnetic field (e.g., CARTO, AURORA®, NIOBE®, or another suitable field, may be referred to generically as "localization fields," while the elements generating the fields, such as surface electrodes 12, 14, 16, 18, 19, and 22 may be generically referred to as "localization field generators." As described above, surface electrodes 12, 14, 16, 18, 19, and 22 may also function as detectors to measure the characteristics of the localization field (e.g., the voltages measured at roving electrodes 17, 52, 54, 56, or a current from roving electrodes 17, 52, 54, 56), and thus may also be referred to as "localization elements." Though the present invention will be described primarily in the context of a localization system that generates an electrical field, one of ordinary skill in the art will understand how to apply the principles disclosed herein in other types of localization fields, and in particular other types of non-ionizing localization fields (e.g., by replacing electrodes 17, 52, 54, 56 with coils to detect different components of a magnetic field).

Localization of catheter 13 can be accomplished as follows. As described above and as illustrated in FIG. 2, catheter 13 includes at least three non-colinear localization electrodes (e.g., electrodes 17, 52, 54, and 56) or other localization elements mounted thereon. Once placed in the non-ionizing localization field generated by localization field generators 12, 14, 16, 18, 19, and 22, three adjacent localization electrodes may be selected. Preferably, the selected three localization elements includes a proximal ring localization electrode, a distal ring localization electrode, and an intermediate spot localization electrode approximately midway between the proximal and distal ring electrodes. Advantageously, such a configuration may be achieved by simply adding spot electrodes approximately midway between adjacent ring electrodes on an existing, clinically accepted device. In FIG. 2, these spot electrodes are denoted by reference numerals 60, 62, and 64. Spot electrodes 60, 62, and 64 can be arranged in many different formats, including linearly along the surface of catheter 13, helically arranged on catheter 13, arranged around the circumference of catheter 13, or any other advantageous arrangement.

With reference to FIG. 2, and for purposes of the following discussion, the selected three electrodes will be distal ring electrode 52, proximal ring electrode 54, and intermediate spot electrode 62. It should be understood, however, that the selected spot electrode need not be intermediate distal ring electrode 52 and proximal ring electrode 54, but rather may be "outside" the pairing of ring electrodes 52, 54 (e.g., spot electrode 60 or spot electrode 64).

Preferably, the selected electrodes are at least about 1 mm apart, and more preferably at least about 2 mm apart, in order to permit distinct measurement of each electrode within the localization field. If the electrodes are sufficiently close together, it is contemplated that catheter 13 may be assumed to be a locally rigid body for purposes of this invention. If the electrodes are further apart, or if catheter 13 is very soft and flexible, however, a rigid body assumption need not be used. Instead, local curvature may be estimated.

Suitable spot electrodes have a diameter that is about ⅛ of the circumference of catheter 13 on which they are mounted. For example, if catheter 13 is a 7 French catheter (e.g., a catheter having an outer diameter of about 2.3 mm), the spot electrodes mounted thereon should have diameters of about 0.9 mm.

Next, the non-ionizing localization field is used to measure a location of each of the selected localization electrodes (or other localization elements) 52, 54, and 62 as described above, which provides position information for catheter 13 within the localization field. One of ordinary skill in the art will appreciate that, for a ring electrode, such a measurement will typically determine the center point of the ring electrode. One of ordinary skill in the art will also appreciate that, for a spot electrode mounted on a non-conducting catheter shaft, the non-conducting shaft may impact the measured location of the spot electrode. In particular, though the spot electrode is mounted on the shaft, the apparent location of the spot electrode may be projected out normally from the shaft by a distance between about 1.7 times to about 2 times the shaft radius depending on the size of the spot electrode. As described in further detail below, this can be addressed by projecting the apparent location of the spot electrode normally back to the shaft surface.

The measured locations of the selected localization electrodes 52, 54, 62 may then be used to construct a three-dimensional representation of catheter 13. The measured location of the spot electrode 62 may be used to determine the rotational attitude of the three-dimensional representation of catheter 13. This three-dimensional representation of catheter 13 within the localization field may then be displayed (e.g., on display 23).

One method of rotationally orienting the three-dimensional representation of catheter 13 is as follows. First, a cylinder is fit to the measured locations of the selected localization electrodes 52, 54, 62. In preferred embodiments of the invention, the cylinder is fit to the measured locations by defining a cylinder having an axis connecting the measured locations of the distal and proximal ring localization electrodes 52, 54 and a diameter equal to the diameter of catheter 13. This axis is referred to herein as the "central axis" or "first axis." Alternatively, the measured locations of the selected localization electrodes 52, 54, 62 may be used to define a "best fit" cylinder.

The cylinder, of course, generally reflects the position of catheter 13 within the localization field. It should be understood that the cylinder fit to the measured locations of the selected localization electrodes need not be a right circular cylinder. It is expressly contemplated that, in some embodiments of the invention, for example where the distal and proximal localization electrodes are sufficiently far apart and/or the catheter is sufficiently soft and flexible to suggest against a rigid body assumption, the cylinder may be curved to approximate local curvature of catheter 13. Cylinder-like shapes, such as oblate spheroids and similar shapes, are also regarded as within the scope of the term "cylinder" for purposes of the invention.

Once the cylinder has been fit to the measured location of the selected localization electrodes, the rotational attitude of the cylinder can be determined. First, the measured location of one of the selected localization electrodes, preferably the measured location of intermediate spot electrode 62, can be orthogonally projected to the surface of the cylinder. An orienting stripe may then be defined parallel to the central axis of the cylinder and passing through the projected location of intermediate spot electrode 62.

When displayed, the orienting stripe informs a user as to which direction intermediate spot electrode 62 is facing, and therefore allows the user to identify the rotational attitude of catheter 13 within the localization field (e.g., it allows the user to determine which side of the catheter is "up"). This is desirable, for example, where the relationship between intermediate spot electrode 62 and the pull wire is known. For example, if intermediate spot electrode 62 is placed directly over the pull wire during manufacture, then the practitioner will know that catheter 13 will deflect in the direction of the orienting stripe when actuated.

It may be costly, however, to precisely place spot electrodes in this fashion during manufacture. Thus, one aspect of the present invention permits calibration of an arbitrarily manufactured catheter 13 (that is, a catheter where the relationship between the electrodes and the pull wires is not known or precisely controlled during manufacture). First, catheter 13 is actuated to deflect through the use of a suitable actuator. The deflected locations of at least distal and proximal ring localization electrodes 52, 54 (and, in some embodiments, of all of the selected localization electrodes) are then measured and used to identify the plane along which catheter 13 has deflected.

In the preferred embodiments of the invention, a new cylinder is fit to the measured deflected locations of the selected localization electrodes, such as by defining an axis, referred to herein as the "deflected axis" or the "second axis" connecting the measured deflected locations of distal and proximal ring localization electrodes 52, 54. Of course, as with the cylinder fit to the undeflected measured locations of localization electrodes 52, 54, 52, the cylinder fit to the deflected locations thereof not be a right circular cylinder.

A deflection plane may then be defined using the first and second axes (e.g., the central and deflected axes), for example by identifying a plane containing both the first and second axes or by defining a best fit plane to the first and second axes. A deflection plane stripe may then be defined on the surface of the three-dimensional representation, typically by defining a deflection plane stripe where the deflection plane intersects the surface of the cylinder fit to the undeflected measured locations of the selected localization electrodes 52, 54, 62. One of ordinary skill in the art will appreciate that the deflection plane will likely intersect this cylinder in two locations; the relationship between the undeflected measured locations and the deflected measured locations of the selected localization electrodes may be used to determine which of the two intersections is the appropriate intersection to mark with the deflection plane stripe.

The purpose of the deflection plane stripe is similar to the purpose of the orienting stripe described above-when displayed, it allows the user to identify how catheter 13 will deflect when actuated in a particular fashion. To further aid the user, a corresponding reference marking may be made on the actuator itself. For example, consider a robotically controlled catheter where the actuator is a joystick. The practitioner may push the joystick "up," resulting in a particular deflection of catheter 13. A colored deflection plane stripe may be drawn on the three-dimensional representation, and a corresponding colored reference marking may be drawn on the actuator in the "up" position. This process may be repeated to define a plurality of deflection plane stripes for a plurality of user-defined deflection planes (e.g., four planes separated by about 90 degrees in a four pull wire device).

Advantageously, these user-defined deflection planes may be arbitrary. That is, by using the present invention, the user need not know where the pull wires are in order to calibrate catheter 13 (e.g., the user need not push the joystick in a direction that the user knows to correspond to only a single pull wire). Nor must the practitioner engage in a trial and error process to relate inputs and outputs—once both the three dimensional representation and the actuator have been suitably marked, the resultant deflection associated with any input may be predicted. Moreover, because this calibration is independent of the localization field in which catheter 13 is to be employed, it need not be carried out within the patient's body during the procedure.

Once catheter 13 is calibrated, it is contemplated that localization system 8 may be used to provide feedback regarding the health of catheter 13. For example, the practitioner can set (e.g., using computer system 20) deflection and/or orientation limits that reflect the expected range of manipulation for catheter 13. Alternatively, these limits may be preset based on the calibration of catheter 13. If localization system 8 indicates that a limit has been exceeded, it may be an indication that catheter 13 has been damaged, and the practitioner may therefore visually inspect catheter 13.

The methods described above may be executed by one or more computer systems (e.g., computer system 20), and may be software implemented (e.g., one or more software programs executed by one or more computer systems or processors), hardware implemented (e.g., a series of instructions stored in one or more solid state devices), or a combination of both. The computer may be a conventional general purpose computer, a special purpose computer, a distributed computer, or any other type of computer. Further, the computer may comprise one or more processors, such as a single central processing unit or a plurality of processing units, commonly referred to as a parallel processing environment. The term "processor" as used herein refers to a computer microprocessor and/or a software program (e.g., a software module or separate program) that is designed to be executed by one or more microprocessors running on one or more computer systems.

For example, a system for localizing a medical device may include: at least one localization field generator for creating a localization field that can be used for determining a location of an object within the localization filed; a localization sheath having at least three non-colinear localization elements mounted thereon; and a localization processor. The localization processor may: measure a location of three or more of the non-colinear localization elements, including at least one spot localization element; construct a three-dimensional representation of a medical device using the measured location of the three or more non-colinear localization elements; and rotationally orient the three-dimensional representation using the measured location of the at least one spot localization element. The system may also include a display to output the three-dimensional representation of the medical device within the localization field.

While catheter 13 is depicted as including localization electrodes thereon, this is not the case with all medical devices. Some medical devices, such as ultrasound intracardiac echocardiography (ICE) catheters, transseptal needles, and gene therapy delivery catheters, lack pre-existing localization elements. Because it is desirable to be able to localize such devices, another aspect of the present invention is a localization sheath that endows an elongate medical device with localization elements.

Figure 3:
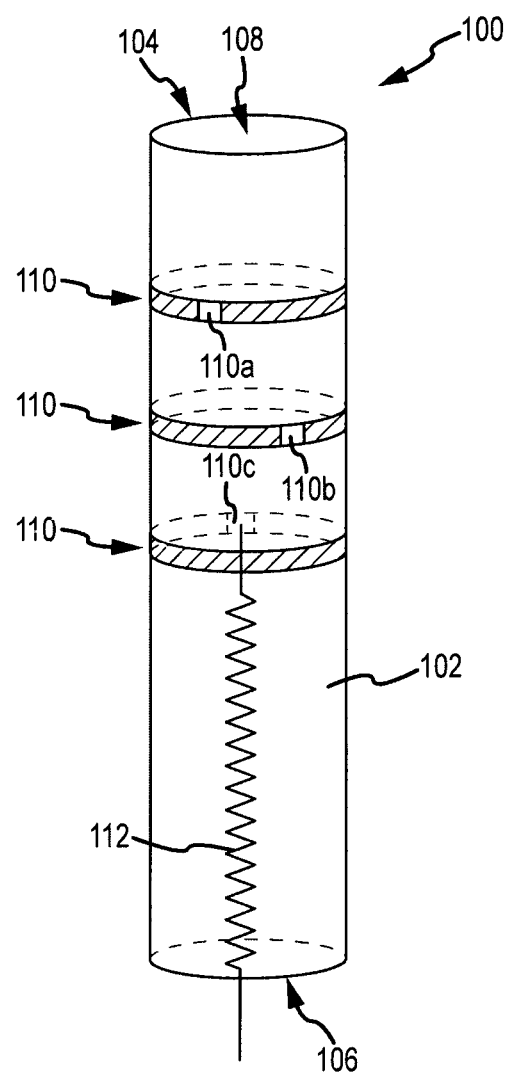
FIG. 3 depicts one embodiment of a localization sheath according to the present invention.
Figure 4A:
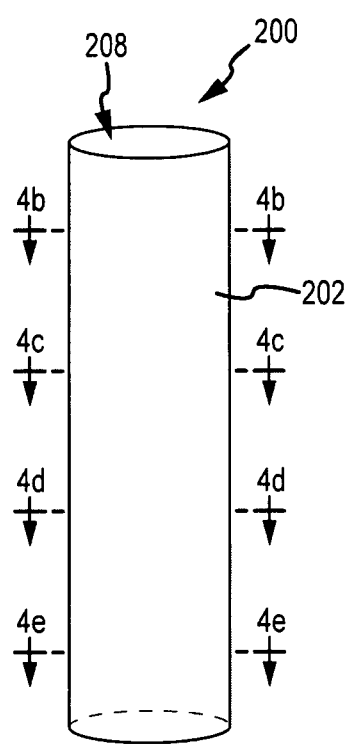
FIG. 4a depicts another embodiment of a localization sheath according to the present invention.
Figure 4B:
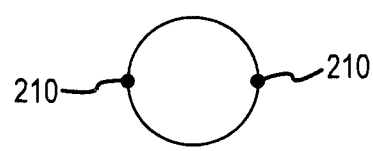
FIGS. 4b-4e are, respectively, cross-sections of the localization sheath of FIG. 4a taken along lines 4b-4b through 4e-4e.
Figure 4C:
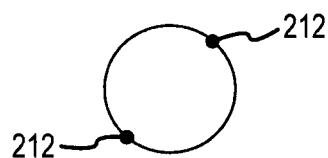
Figure 4D:
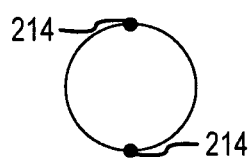
Figure 4E:
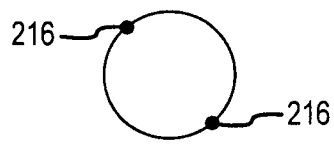

FIG. 3 illustrates a localization sheath 100 according to this aspect of the invention. Localization sheath 100 includes an elongate, flexible sheath body 102 having an open distal end 104 and an open proximal end 106. Sheath body 102 defines a lumen 108 sized to conformably receive an elongate medical device that need not include its own localization elements.

Mounted on sheath body 102 are a plurality of localization elements 110. FIG. 3 illustrates three non-colinear localization elements 110, but it should be understood that more than three such elements may be used without departing from the sprit and scope of the present invention. For example, additional localization elements 110 may be provided to enhance the three-dimensional representation of the medical device received within lumen 108.

Localization elements 110 are illustrated as ring electrodes. However, portions of the ring electrodes have been insulated such that only three spot electrodes 110*a*, 110*b*, 110*c* are electrically active. Of course, the localization elements may be ring electrodes, spot electrodes, partially masked ring electrodes, or any combination thereof, without departing from the spirit and scope of the present invention.

Localization elements 110 are connected to leads 112 (only one of which is shown for clarity) that extend proximally to one or more suitable connectors. To accommodate bending and torquing of the medical device received within lumen 108, leads 112 may be zig-zagged along the length of sheath body 102 such that they flex to accommodate the expansion and contraction associated with bending and torquing of the medical device received within lumen 108. One or more suitable connectors (not shown) may be provided to connect leads 112 to a localization system.

Sheath body 102 is preferably compliant so as to allow unimpeded deflection of the medical device received within lumen 108. Suitable materials include polyether block amides (e.g., PEBAX® having a Shore-D hardness between about 30D and about 45D), silicone, polyurethane, polytetrafluoroethylene (PTFE) (e.g., TEFLON®), and any combinations thereof.

In some embodiments of the invention, sheath body 102 includes an inner layer and an outer layer. Localization elements 110 and leads 112 may be sandwiched between the inner layer and the outer layer, for example by bonding the inner layer and outer layer to each other via reflow bonding, heat shrinking, heat staking, or the like. Of course, other methods of mounting localization elements 110 to sheath body 102 are contemplated. It is also contemplated that the localization elements 110 and leads 112 may first be assembled on relatively rigid tubing or a mandrel and then placed on sheath body 102.

An alternative embodiment of a localization sheath 200 is depicted in FIGS. 4*a*-4*e*. Localization sheath 200 is especially desirable for use in connection with soft and flexible catheters for which the assumption of a locally rigid body might be an oversimplification. Localization sheath 200 utilizes a plurality of non-colinear spot electrodes arranged in substantially uniformly spaced "layers" along the length of sheath body 202 to permit estimation of local curvature and orientation of the medical device received within lumen 208. As illustrated in FIGS. 4*b*-4*e*, each "layer" includes a pair of opposing spot electrodes (e.g., 210/210, 212/212, 214/214, 216/216), with each pair having a unique rotational orientation so as to ensure non-colinearity between any three selected pairs of opposing spot electrodes. Of course, spot electrodes 210, 212, 214, 216 and their associated leads (not shown) may be mounted to sheath body 202 as described above (e.g., by sandwiching them between two layers that are then bonded to each other).

In use, an elongate medical device may be placed within localization sheath 100 or 200 so that localization sheath 100 or 200 may be affixed thereto. Once affixed, localization sheath 100 or 200 should not move relative to the medical device received therein, but should instead be conformably attached such that it mimics the movement thereof (e.g., when the medical device deflects, the localization sheath deflects; when the medical device rotates, the localization sheath rotates; when the medical device torques, the localization sheath torques). This permits medical devices to be rapidly, reliably, and economically endowed with localization capability.

In some embodiments, the localization sheath is affixed to the medical device by first softening the localization sheath with a solvent and then evaporating the solvent after placing the elongate medical device within the localization sheath. As the solvent is evaporated, the localization sheath contracts and becomes bound to the medical device.

In other embodiments, the localization sheath is affixed to the medical device through the use of an adhesive, such as an ultraviolet-activated adhesive.

In still other embodiments, the localization sheath is affixed to the medical device via the application of heat to bond the localization sheath to the medical device.

Although several embodiments of this invention have been described above with a certain degree of particularity, those skilled in the art could make numerous alterations to the disclosed embodiments without departing from the spirit or scope of this invention.

For example, though the invention has been described in connection with only a single set of three adjacent non-colinear localization elements, one of ordinary skill in the art would appreciate that multiple sets of three adjacent non-colinear localization elements could be selected to enhance the three-dimensional representation. For example, the methods disclosed herein could be applied to the following sets of electrodes in constructing a localized three-dimensional representation of catheter 13: 17, 60, 52; 52, 62, 54; and 54, 64, 56.

As another example, the localization sheath could take the form of an introducer catheter used to introduce other medical devices into the patient's body.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of localizing a medical device, the method comprising:
    providing an elongate medical device having a diameter and at least three non-colinear localization electrodes mounted thereon;
    placing the elongate medical device within a non-ionizing localization field;
    selecting three adjacent localization electrodes of the at least three non-colinear localization electrodes, the selected three localization electrodes including a proximal ring localization electrode, a distal ring localization electrode, and a third localization electrode;
    using the non-ionizing localization field to measure a location of each of the selected three localization electrodes;
    defining a cylinder having a central axis connecting the measured locations of the proximal and distal ring localization electrodes and a diameter equal to the diameter of the elongate medical device;
    projecting the measured location of the third localization electrode orthogonally to a surface of the defined cylinder;
    defining an orienting stripe parallel to the central axis of the defined cylinder and passing through the projected location of the third localization electrode; and
    constructing a three-dimensional representation of the elongate medical device within the localization field.

2. The method according to claim 1, wherein the third localization electrode comprises an intermediate localization electrode positioned between the proximal ring electrode and the distal ring electrode.

3. The method according to claim 1, wherein the step of providing an elongate medical device comprises:
    providing an elongate medical device;
    providing a localization sheath having at least three non-colinear localization electrodes mounted thereon; and
    placing the elongate medical device within the localization sheath.

4. The method according to claim 3, further comprising affixing the localization sheath to the elongate medical device.

5. The method according to claim 4, wherein the step of affixing the localization sheath to the medical device comprises:
    expanding and softening the localization sheath using a solvent prior to placing the elongate medical device within the localization sheath; and
    evaporating the solvent after placing the elongate medical device within the localization sheath.

6. The medical device according to claim 4, wherein the step of affixing the localization sheath to the medical device comprises bonding the localization sheath to the medical device via an ultraviolet-activated adhesive.

7. The medical device according to claim 4, wherein the step of affixing the localization sheath to the medical device comprises laminating the localization sheath to the medical device via the application of heat.

8. The method according to claim 3, wherein the localization sheath includes at least one actuator configured to deflect the localization sheath along at least one plane.

9. The method according to claim 1, wherein the elongate medical device includes at least one actuator configured to deflect the elongate medical device along at least one plane.

10. The method according to claim 9, further comprising:
    actuating the elongate medical device to deflect;
    measuring a deflected location of each of the proximal and distal ring localization electrodes;
    defining a deflected axis connecting the measured deflected locations of the proximal and distal ring localization electrodes;
    defining a deflection plane using the central axis of the defined cylinder and the deflected axis; and
    defining a deflection plane stripe where the deflection plane intersects the surface of the defined cylinder.

11. The method according to claim 10, further comprising marking the at least one actuator with a reference corresponding to the deflection plane.

12. The method according to claim 11, further comprising displaying the deflection plane stripe as part of the three-dimensional representation of the elongate medical device within the localization field, wherein the displayed deflection plane stripe corresponds to the marking on the at least one actuator.

13. The method according to claim 1, further comprising repeating the steps of:
    actuating the elongate medical device to deflect;
    measuring a deflected location of each of the proximal and distal ring localization electrodes;
    defining a deflected axis connecting the measured deflected locations of the proximal and distal ring localization electrodes;
    defining a deflection plane using the central axis of the defined cylinder and the deflected axis; and defining a deflection plane stripe where the deflection plane intersects the surface of the defined cylinder to define a plurality of deflection plane stripes for a plurality of user-defined deflection planes.

14. The method according to claim 1, further comprising displaying the three-dimensional representation of the elongate medical device within the localization field.

15. The method according to claim 1, wherein the step of using the non-ionizing localization field to measure a location of each of the selected three localization electrodes comprises determining a position of a center of the proximal ring localization electrode and a position of a center of the distal ring localization electrode.

16. A method of localizing a medical device, the method comprising:
providing an elongate medical device having at least three non-colinear localization elements mounted thereon;
placing the elongate medical device within a non-ionizing localization field;
selecting three or more of the non-colinear localization elements, wherein at least one of the selected non-colinear localization elements is a spot localization element;
using the non-ionizing localization field to measure a location of each of the selected non-colinear localization elements;
constructing a three-dimensional representation of the elongate medical device using the measured location of each of the selected non-colinear localization elements; and
rotationally orienting the three-dimensional representation of the elongate medical device using the measured location of the spot localization element.

17. The method according to claim 16, wherein the step of constructing a three-dimensional representation of the elongate medical device comprises fitting a cylinder to the measured location of each of the selected non-colinear localization elements, wherein the cylinder fit to the measured location of each of the selected non-colinear localization elements has a first axis.

18. The method according to claim 17, wherein:
the selected non-colinear localization elements include a distal ring electrode and a proximal ring electrode; and
the step of fitting a cylinder comprises defining a cylinder having a central axis connecting the measured locations of the distal ring electrode and the proximal ring electrode and a diameter equal to a diameter of the elongate medical device.

19. The method according to claim 17, wherein the elongate medical device includes at least one actuator configured to deflect the elongate medical device along at least one plane, further comprising:
actuating the elongate medical device to deflect;
measuring a deflected location of each of the selected non-colinear localization elements;
defining a deflection plane using the measured location and the measured deflected location of each of the selected non-colinear localization elements; and
defining a deflection plane stripe on the surface of the three-dimensional representation of the elongate medical device.

20. The method according to claim 19, wherein the step of defining a deflection plane comprises:
fitting a cylinder to the measured deflected location of each of the selected non-colinear localization elements, wherein the cylinder fit to the measured deflected location of each of the selected non-colinear localization elements has a second axis; and
defining a deflection plane using the first axis and the second axis.

21. The method according to claim 20, wherein the step of defining a deflection plane stripe comprises defining a deflection plane stripe where the deflection plane intersects the cylinder fit to the measured location of each of the selected non-colinear localization elements.

22. The method according to claim 19, further comprising marking the at least one actuator with a reference corresponding to the deflection plane.

23. The method according to claim 16, wherein the step of providing an elongate medical device comprises:
providing an elongate medical device;
providing a localization sheath having at least three non-colinear localization elements mounted thereon;
placing the elongate medical device within the localization sheath; and
affixing the localization sheath to the elongate medical device.

24. The method according to claim 16, wherein the step of rotationally orienting the three-dimensional representation comprises defining an orienting stripe on a surface of the three-dimensional representation through the measured location of the spot localization element.

* * * * *